US00PP08873P

United States Patent [19]

Blanken

[11] Patent Number: Plant 8,873

[45] Date of Patent: Aug. 30, 1994

[54] *ILEX AQUIFOLIUM* — LIMSI CULTIVAR

[75] Inventor: Arie Blanken, Boskoop, Netherlands

[73] Assignee: The Conard-Pyle Company, West Grove, Pa.

[21] Appl. No.: 139,725

[22] Filed: Oct. 22, 1993

[51] Int. Cl.[5] ..... A01H 5/00

[52] U.S. Cl. ..... Plt./65

[58] Field of Search ..... Plt. 65

*Primary Examiner*—James R. Feyrer

*Attorney, Agent, or Firm*—Burns, Doane, Swecker & Mathis

[57] ABSTRACT

A new and distinct variety of *Ilex aquifolium* which originated as a chance seedling in a cultivated area is provided. The new variety is well-suited for growing as attractive ornamentation in the landscape where it exhibits a naturally pyramidal upright growth habit that well retains such configuration following pruning. The dark green leaves exhibit a good luster on upper surface, are somewhat variable in shape, and the spines present thereon tend not to catch the clothing. Highly visible bright red berries are formed in abundance. Additionally, excellent cold tolerance is exhibited.

1 Drawing Sheet

SUMMARY OF THE INVENTION

The new cultivar of the present invention was discovered and selected by me as a chance seedling of *Ilex aquifolium* while being grown among many other plants under my direction in a cultivated area of the nursery of Kwekerij de Limieten in The Netherlands. The pollen parent is unknown since open pollination had been utilized.

It was an object of the selection process which resulted in the new cultivar to provide an improved female cultivar of *Ilex aquifolium* that exhibits improved hardiness, an upright growth habit, the heavy bearing of attractive fruit, and the ability to fulfill a wide variety of landscape needs. This goal was met in the selection of the present cultivar. Had the new cultivar of the present invention not been discovered and preserved by me it would have been lost to mankind.

It was found that the new female *Ilex aquifolium* cultivar of the present invention possesses the following combination of characteristics:

(a) forms an attractive densely-formed naturally pyramidal upright evergreen shrub or small tree with a vigorous head branch that well retains such pyramidal configuration following pruning,
(b) forms dark green leaves of variable shape having a good luster on the upper surface and which bear spines that lack a propensity to catch clothing,
(c) forms pistillate flowers primarily during the first half of May when grown in southeastern Pennsylvania,
(d) forms in abundance highly-visible bright red berries, and
(e) exhibits a cold tolerance that substantially exceeds that of the Pyramidalis and J. C. Van Tol cultivars of *Ilex aquifolium.*

The new cultivar has been found to be particularly suited for growing as highly attractive ornamentation in the garden or landscape.

As indicated, the new cultivar of the present invention exhibits excellent winter hardiness. For instance, it has overwintered well when planted in the open landscape as well as when planted in containers above the ground at West Grove, Pa., U.S.A., which is present in USDA Zone 6. The new cultivar has well withstood winter temperatures of −20° C.

Asexual reproduction of the new variety by cuttings has been carried out at The Netherlands and at West Grove, Pa., U.S.A. This has demonstrated that the unique combination of characteristics is stable and is transmitted to successive generations.

When the new cultivar is compared to the previously available J. C. Van Tol cultivar (non-patented in the United States) of *Ilex aquifolium,* it is found that the new cultivar better maintains its pyramidal configuration following pruning, has a more vigorous head or lead branch, forms dark green irregular foliage that varies in shape on the same plant, forms more abundantly large bright red berries that are highly visible, and exhibits superior tolerance to low winter temperatures.

While it cannot be predicted with certainty, it is estimated that the new cultivar when fully mature will assume a height of approximately 5 to 6 meters.

The new cultivar has been named the Limsi cultivar.

BRIEF DESCRIPTION OF THE PHOTOGRAPHS

The accompanying photographs show as nearly true as it is reasonably possible to make the same, in a color illustration of this character, typical specimens of the new cultivar. The plants illustrated herein were photographed on Sep. 20, 1990 while growing at Huizen, The Netherlands.

FIG. 1 illustrates a plant of the LIMSI cultivar of approximately 20 years of age having a height of approximately 2.5 meters. The plant has been pruned often in order to collect cuttings. The abundantly formed large bright red berries are clearly visible.

FIG. 2 illustrates a close-up view of representative foliage and berries present on the plant of FIG. 1.

DETAILED DESCRIPTION

Figure 1:
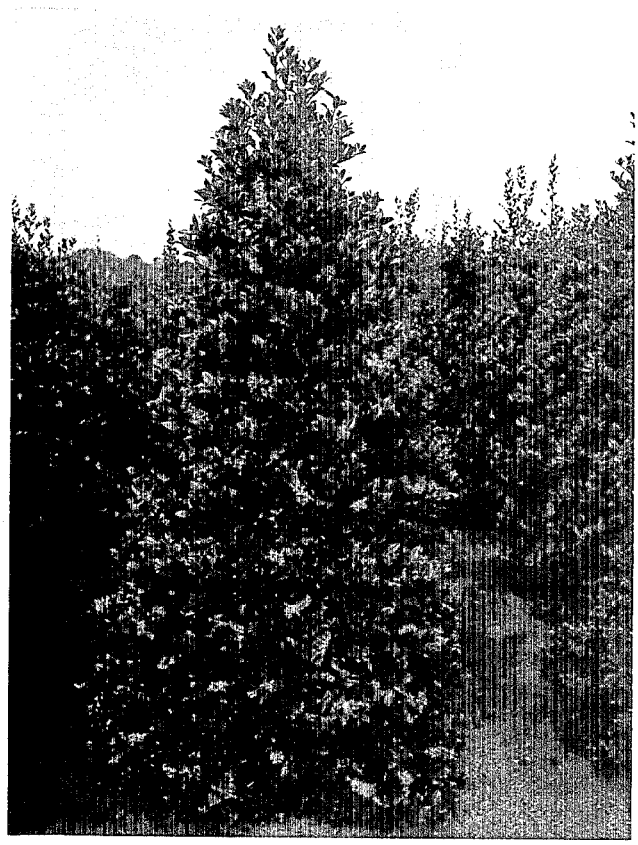
Figure 2:
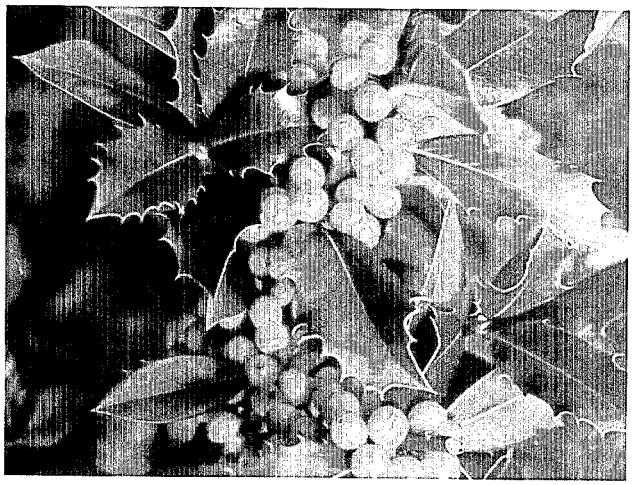

The chart used in the identification of the colors is that of The Royal Horticultural Society (R.H.S. Colour Chart). The description is based upon the observation of three-year-old plants growing in containers above the ground at West Grove, Pa., U.S.A.

Class: Hardy, broad, upright, evergreen shrub or small tree for garden decoration and general landscape use.

Parentage: *Ilex aquifolium.*

Foliage:

*Type.*—Evergreen. Leaves are elliptic with an acuminate tip. The shape, size, and quantity of spines are highly variable with the age of the foliage and location on the plant.

*Leaf margins.*—Spiny and undulating. The number of spines per leaf commonly varies from 1 to approximately 14. There is always a single spine at the leaf apex. The current year's growth may or may not have additional spines. The spines tend not to catch or snag clothing to any substantial degree when contact is made.

*Leaf size.*—Length: approximately 5 to 8 cm. on average when measured to the tip of the spine at the apex. Width: approximately 3 to 5 cm. on average at the widest point when measured to the tips of spines (if present).

*Petiole.*—Length: approximately 9 mm. on average. Color: commonly between Yellow-Green Group 146B and Yellow-Green Group 146C.

*Leaf color.*—On young leaves: when grown outdoors in containers during May commonly between Green Group 139A and Yellow-Green Group 147A on the upper side, and Yellow-Green Group 146A on the lower side. On mature leaves: when grown outdoors in containers during May between Green Group 139A and Yellow-Green Group 147A on the upper side, and Yellow-Green Group 146B on the lower side.

*Stems.*—Young stems: approaching Yellow-Green Group 148A, and strongly tinged with purple. Mature stems: approaching Green Group 137C, and more or less strongly tinged with purple.

Inflorescence:

*Form.*—Pistillate flowers commonly are borne several per stem in clusters of 3 to 5 on average on medium stems of the prior year's growth. Such flowers are typical female flowers of the species, and are borne freely when the plant is present outdoors.

*Peduncle.*—The flowers are borne on light green smooth peduncles of Yellow-Green Group 143C.

*Bud.*—Before the calyx opens the size is small. Such buds are short and globular without foliaceous appendages. As the calyx opens, the color is white and is strongly stained with reddish-green coloration. As the first petal opens, the buds are typical of the genus and approximate White Group 155B stained with greenish coloration on the inside and on the outside.

*Bloom.*—Size: approximately 1 cm. in diameter. Color: White Group 155B on the upper side and White Group 155C on the lower side.

*Berries.*—Shape: round, approximately 8 to 10 mm. in diameter. Quantity: very abundant (as illustrated). Color: Red Group 45A.

I claim:

1. A new and distinct female *Ilex aquifolium* cultivar possessing the following characteristics:

(a) forms an attractive densely-formed naturally pyramidal upright evergreen shrub or small tree with a vigorous head branch that well retains such pyramidal configuration following pruning, (b) forms dark green leaves of variable shape having a good luster on the upper surface and which bear spines that lack a propensity to catch clothing, (c) forms pistillate flowers primarily during the first half of May when grown in southeastern Pennsylvania, (d) forms in abundance highly-visible bright red berries, and (e) exhibits a cold tolerance that substantially exceeds that of the Pyramidalis and J. C. Van Tol cultivars of *Ilex aquifolium;* substantially as herein shown and described.

* * * * *